(12) United States Patent  (10) Patent No.: US 7,947,010 B2
Arscott, II et al.  (45) Date of Patent: May 24, 2011

(54) COMPOSITION AND SYSTEM FOR WOUND DECONTAMINATION

(75) Inventors: Edward F. Arscott, II, Warsaw, IN (US); Mark A. Heldreth, Mentone, IN (US)

(73) Assignee: DePuy Products, Inc., Warsaw, IN (US)

( * ) Notice: Subject to any disclaimer, the term of this patent is extended or adjusted under 35 U.S.C. 154(b) by 1161 days.

(21) Appl. No.: 11/428,674

(22) Filed: Jul. 5, 2006

(65) Prior Publication Data

US 2007/0009505 A1 Jan. 11, 2007

Related U.S. Application Data

(60) Provisional application No. 60/697,658, filed on Jul. 8, 2005.

(51) Int. Cl.
*A61M 1/06* (2006.01)
(52) U.S. Cl. .......................................................... 604/73
(58) Field of Classification Search .................... 604/73, 604/82, 131, 289, 518
See application file for complete search history.

(56) References Cited

U.S. PATENT DOCUMENTS

| | | | |
|---|---|---|---|
| 2,129,264 A | 9/1938 | Downing et al. | |
| 2,944,902 A | 7/1960 | Carroll et al. | |
| 3,349,032 A | 10/1967 | Krieg | |
| 3,954,633 A | 5/1976 | Dollinger et al. | |
| 4,110,263 A | 8/1978 | Lindemann et al. | |
| 4,181,634 A | 1/1980 | Kennedy et al. | |
| 4,489,750 A | 12/1984 | Nehring | |
| 4,561,432 A | 12/1985 | Mazor | |
| 4,635,621 A | 1/1987 | Atkinson | |
| 4,655,197 A | 4/1987 | Atkinson | |
| 4,662,829 A | 5/1987 | Nehring | |
| 4,741,678 A | 5/1988 | Nehring | |
| 4,892,526 A | 1/1990 | Reese | |
| 4,941,872 A | 7/1990 | Felix et al. | |
| 5,059,187 A | 10/1991 | Sperry et al. | |
| 5,071,104 A | 12/1991 | Witt et al. | |
| 5,133,701 A | 7/1992 | Han | |
| 5,277,901 A | 1/1994 | Vigh et al. | |
| 5,300,787 A | 4/1994 | Schrauwen et al. | |
| 5,322,506 A | 6/1994 | Kullas | |
| 5,419,772 A | 5/1995 | Teitz et al. | |
| 5,470,305 A | 11/1995 | Arnett et al. | |
| 5,487,649 A | 1/1996 | Dorsey, III et al. | |
| 5,489,280 A * | 2/1996 | Russell | 604/311 |
| 5,512,597 A | 4/1996 | Kyba et al. | |
| 5,520,667 A | 5/1996 | Roche | |
| 5,536,494 A | 7/1996 | Park | |
| 5,603,929 A | 2/1997 | Desai et al. | |
| 5,630,793 A * | 5/1997 | Rowe | 604/20 |
| 5,653,972 A | 8/1997 | Desai et al. | |
| 5,718,668 A | 2/1998 | Arnett et al. | |
| 5,746,721 A | 5/1998 | Pasch et al. | |
| 5,792,108 A | 8/1998 | Felix et al. | |
| 5,814,022 A * | 9/1998 | Antanavich et al. | 604/191 |
| 5,830,197 A | 11/1998 | Rucinski | |
| 5,924,448 A | 7/1999 | West | |
| 5,941,851 A | 8/1999 | Coffey et al. | |
| 5,957,928 A | 9/1999 | Kirwan, Jr. | |

(Continued)

*Primary Examiner* — Nicholas D Lucchesi
*Assistant Examiner* — Aarti B Berdichevsky
(74) *Attorney, Agent, or Firm* — Barnes & Thornburg LLP (57) ABSTRACT

The present disclosure is directed to a cleansing solution and system for administering the cleansing solution to decontaminate a wound surface. A method and kit for decontaminating a wound surface is also provided.

6 Claims, 4 Drawing Sheets

U.S. PATENT DOCUMENTS

| | | |
|---|---|---|
| 6,022,329 A | 2/2000 | Arnett et al. |
| 6,051,611 A | 4/2000 | Kyba et al. |
| 6,059,754 A | 5/2000 | Pasch et al. |
| 6,375,973 B2 | 4/2002 | Yanni |
| 6,520,931 B2 * | 2/2003 | Suh .................................. 604/73 |
| 6,559,189 B2 | 5/2003 | Baker, Jr. et al. |
| 6,884,230 B1 * | 4/2005 | Epstein et al. .................... 604/82 |
| 7,425,209 B2 * | 9/2008 | Fowles et al. .................. 604/415 |
| 2004/0059283 A1 | 3/2004 | Kirwan et al. |
| 2004/0267193 A1 * | 12/2004 | Bagaoisan et al. ............... 604/82 |
| 2005/0148958 A1 * | 7/2005 | Rucinski ......................... 604/290 |
| 2006/0025716 A1 * | 2/2006 | Babaev ............................. 604/22 |

\* cited by examiner

COMPOSITION AND SYSTEM FOR WOUND DECONTAMINATION

This application claims priority to U.S. Provisional Patent Application No. 60/697,658, filed Jul. 8, 2005, the disclosure of which is hereby incorporated by reference herein.

FIELD OF THE DISCLOSURE

The present disclosure relates to a decontamination composition and a system and method for applying the decontamination composition to a wound surface to decontaminate the surface.

BACKGROUND

Deep wound infections resulting from open wound orthopaedic and trauma procedures are both costly to the health care system and physically (and emotionally) debilitating for the patient. Currently, there are no FDA approved surgical wound irrigants for cleansing surgical wounds and open trauma surfaces, other than sterile saline. Surgeons will prescribe the addition of antibiotics (such as Bacitracin) or a dilute hypochlorite solution (dilute bleach) in an effort to improve the cleansing capabilities of sterile saline irrigants. However, surgeons will also agree that there is little science behind this custom, with the effectiveness of antibiotics delivered via short term exposure being particularly suspect. It is unlikely that complete bacterial kill is achieved under such conditions and there is no improvement in the solution's ability to remove contamination and bacteria (or endotoxins resulting from dead bacteria) from the surface of the tissue.

There have been some published studies regarding the ad hoc use of commonly available surfactants (such as castille soap) and disinfectants (such as betadine and hydrogen peroxide) applied directly to deep wounds. These studies indicate that some of these approaches can have a negative impact upon wound tissue healing. In Europe, there has been some clinical work with solutions containing a biguanide disinfectant (such as polyhexamethylene biguaninde or PHMB). Indications are that improper use (delivery) or dosage can lead to complications (such as anaphylaxis in rare instances).

Another approach related to managing orthopaedic wounds has been the addition of antibiotics to bone cement. Its widespread prophylactic use in the US is restricted due to concerns regarding development of a resistant bacterial strain in the patient. The FDA has contraindicated use of these products for prophylactic use, limiting it only to use in two stage revisions. In addition, recent guidance from the American Academy of Orthopaedic Surgeons (AAOS) is discouraging wide spread prophylactic use of these products. As with the ad hoc addition to sterile saline, the addition of antibiotics to bone cement, does not result in an improvement to wound cleansing or healing directly related to contamination, bacteria, or bacterial endotoxin, removal.

Current rates of post-operative deep infection vary by surgical procedure, reporting clinician, and hospital. Current estimates, however, are approximately as follows: Primary hip—1%; Revision hip—3%; Primary knee—1.5%; Revision knee—5% (recent information indicates that the infection rate in revision knee surgery has increased significantly in the last two years); Trauma 1M rods—5 to 15%; Trauma Ex-fix pins—15% or greater.

The current standard of care for orthopaedic implants with an established deep infection is a "two-stage" procedure wherein the initial implant is removed, the infection is brought under control over a period of 6-8 weeks, and then a new implant is inserted. With the exception of ex-fix pins, the removal and replacement of the implant entails two complex and potentially challenging surgeries with the patient being in a compromised condition (either bed ridden or on crutches with braces) for 6 to 8 weeks. The patient is exposed to a traumatic experience and the health care system costs can be in excess of $60,000 (US estimates). In severe situations, re-infection can occur, and sadly, even amputation in relatively rare situations.

Although efforts in the 1980's and 1990's to reduce infection rates associated with total joint replacements have met with success in developed nations, recent trends such as the increase in infection rates associated with revision knee procedures is a reason for concern. It has been speculated that this trend could be due to less experienced surgical staffs (as the need to manage increasing numbers of revision cases grows) and the rise of resistant organisms such as methycillin resistant staph. Infection rates associated with surgery are significantly higher in developing nations. As total joint surgery expands into developing countries, a robust, yet easily deployed, wound cleansing program will be a major part of the successful adoption of joint replacement in those markets.

The clinical need for satisfactory wound cleansing and healing in open (compound fracture) trauma situations is universal world wide. In many cases the delay between the event and proper wound management/stabilization prior to musculoskeletal reconstruction can be several hours. These situations provide a significant challenge for wound decontamination, which is still debated at major orthopaedic trauma meetings. As such, there is clinical need for a satisfactory composition, and system for delivering that composition to a wound site, wherein the composition effectively neutralizes or removes pathogenic and/or infectious agents upon contact with the wound surface.

SUMMARY

One embodiment is directed to a biocompatible cleansing solution comprising a biocompatible surfactant and a preservative, and a method of using that composition or mixture to decontaminating a wound site. In one embodiment the biocompatible surfactant is selected from the group consisting of polyethylene oxides, polypropylene oxides, polypropylene glycols and polyethylene glycols or co-polymers thereof and the preservative is selected from the group consisting of the biguanide family of compounds, quaternary ammonium compounds and poly quaternary ammonium compounds. In another embodiment the biocompatible cleansing solution comprises a biocompatible surfactant, a preservative, and an enzymatic agent that disrupts microbial produced biofilms.

Another embodiment of the present disclosure is directed to a system for decontaminating a wound site. The system includes a mixer having a first inlet, a second inlet, a mixing chamber positioned downstream from the first and second inlets, and an outlet positioned downstream from the mixing chamber. The system further includes a sterile, biocompatible cleansing solution contained in a first receptacle and a sterile saline solution contained in a second receptacle. The first receptacle is in fluid communication with the first inlet of the mixer and the second receptacle is in fluid communication with the second inlet of the mixer. A diffuser of the system is in fluid communication with the outlet of the mixer.

Illustratively, the mixer may further include a spring-biased valve member movable between a closed position and an opened position. In the closed position, the valve member prevents fluid communication between the mixing chamber and the first and/or second inlets to prevent the sterile, biocompatible cleansing solution and/or the sterile saline solution from entering the mixing chamber. In the opened position, the valve member permits fluid communication between the mixing chamber and the first and second inlets to permit the sterile, biocompatible solution and the sterile saline solution to enter the mixing chamber.

The valve member may include a cone-shaped diverter to close the second inlet when the valve member is in the closed position. A flange of the valve member may extend outwardly from the diverter to close the first inlet when the valve member is in the closed position.

Further illustratively, the mixer may include a valve housing having an annular plenum defining an annular space and a mixing conduit coupled to the annular plenum to define the mixing chamber. The first inlet of the mixer may be formed in a front wall of the annular plenum. The annular plenum may include an inner wall defining a central aperture and the central aperture may define the second inlet. The annular plenum may further include a plurality of hollow spokes in fluid communication with the annular space. A rear wall of the annular plenum may define one or more first discharge ports in communication with the mixing chamber. The discharge port(s) may be in fluid communication with the first inlet as well. The annular plenum may further define a second discharge port in fluid communication with the mixing chamber and the second inlet. The second discharge port may be smaller than the second inlet.

According to the present disclosure, the system may further include a bypass valve positioned downstream from the first receptacle to control the rate of flow of the cleansing solution through the first inlet of the mixer.

According to still another aspect of the present disclosure, the diffuser of the system may be configured to dispense fluid at a non-pulsatile pressure of less than 20 dyne/cm$^2$.

According to yet another aspect of the present disclosure, a kit for disinfecting and cleansing a surgical wound may include a biocompatible cleansing solution comprising a surfactant and an antimicrobial agent or a preservative and a sterile mixer. The sterile mixer may include a first inlet, a second inlet, a mixing chamber positioned downstream from the first and second inlets, and an outlet positioned downstream from the mixing chamber. The sterile mixer may further include a valve member positioned between the mixing chamber and the first and second inlets. The valve member may movable between a closed position to prevent fluid flow from the first and second inlets to the mixing chamber and an opened position to permit fluid flow from the first and second inlets to the mixing chamber.

Illustratively, the sterile mixer may further include an annular plenum having (i) the first and second inlet ports defined therein, (ii) a plurality of first discharge outlets in fluid communication with both the first inlet and the mixing chamber, and (iii) a second discharge outlet in fluid communication with both the second inlet and the mixing chamber. The sterile mixer may further include a plurality of vanes provided within the mixing chamber and configured to impart an annular flow on fluid flowing through the mixing chamber. The valve member may include a cone-shaped diverter and a plurality of flanges extending radially from the diverter.

The kit may further include a plurality of sterile, flexible conduit tubing.

According to yet another aspect of the present disclosure, a method of decontaminating a wound surface includes the steps of (i) advancing sterile saline through a mixing chamber at a point of patient care, (ii) advancing a sterile, biocompatible cleansing solution into the mixing chamber at the point of patient care, (iii) mixing the sterile saline and the sterile, biocompatible cleansing solution within the mixing chamber to create a sterile saline/cleansing solution mixture, (iv) advancing the sterile saline/cleansing solution mixture from the mixing chamber through a diffuser, and (v) spraying a wound surface with the sterile saline/cleansing solution mixture.

According to one aspect of this disclosure, the step of advancing the sterile saline may includes (i) advancing the sterile saline around a cone-shaped valve member to divert a flow of the sterile saline outwardly around the valve member, and (ii) moving the valve member from a closed position to prevent flow of the sterile, biocompatible cleansing solution into the mixing chamber to an opened position to permit flow of the sterile saline and the sterile, biocompatible cleansing solution into the mixing chamber.

According to another aspect of this disclosure, the step of advancing the sterile, biocompatible cleansing solution includes advancing the sterile, biocompatible cleansing solution through a first inlet into an annular space upstream from the mixing chamber and out a plurality of first discharge ports into the mixing chamber.

According to yet another aspect of this disclosure, the step of advancing the sterile saline creates a venturi effect to draw the sterile, biocompatible cleansing solution into the mixing chamber.

Illustratively, according to still another aspect of the present disclosure, a receptacle containing the sterile saline, a receptacle containing the sterile, biocompatible cleansing solution, and a diffuser to spray the wound surface with the mixer may each be fluidly coupled to the mixing chamber during the spraying step.

Further illustratively, spraying step may include spraying the wound surface with a non-pulsatile stream of the mixture at an impact pressure of about 8 to about 12 dyne/cm$^2$ and the sterile, biocompatible cleansing solution may include a biocompatible surfactant and a preservative.

DETAILED DESCRIPTION

While the concepts of the present disclosure are susceptible to various modifications and alternative forms, specific exemplary embodiments thereof have been shown by way of example in the drawings and will herein be described in detail. It should be understood, however, that there is no intent to limit the disclosure to the particular forms disclosed, but on the contrary, the intention is to cover all modifications, equivalents, and alternatives following within the spirit and scope of the invention as defined by the appended claims.

One aspect of the present disclosure is directed to a biocompatible cleansing solution for cleansing and decontaminating a wound site or surface. Illustratively, a system 10 for applying the solution to the wound surface includes a mixer 16 to mix the cleansing solution with saline prior to cleansing and decontaminating the wound surface.

In accordance with one embodiment a biocompatible cleansing solution is provided that comprises a biocompatible surfactant and a preservative. The surfactant and the preservative are selected to provide enhanced cleansing (i.e. removal of non-host material and host cellular debris) and disinfection of the wound while using reduced irrigation pressures and volumes. The various cleansing solutions of the present disclosure may be administered to the wound site with a relatively low, continuous pressure while retaining effective cleansing of the wound site. In particular, such low pressure administering of the solution in a non-pulsatile manner may reduce the potential to damage to native tissue during the cleansing of the wound site and, therefore, may provide less negative impact upon wound/bone healing.

In accordance with one embodiment, the biocompatible cleansing solution comprises a surfactant and a preservative, wherein the biocompatible surfactant is selected from the group consisting of polyethylene oxides, polypropylene oxides, polypropylene glycols and polyethylene glycols or co-polymers thereof and the preservative is selected from the group consisting of the biguanide family of compounds, quaternary ammonium compounds and poly quaternary ammonium compounds. In one embodiment the surfactant is co-polymer of two or more compounds selected from the group consisting of polyethylene oxide, polypropylene oxide and polyethylene glycol, and in one embodiment the surfactant is a triblock co-polymer of polypropylene oxide-polyethylene oxide-polypropylene oxide.

In accordance with one embodiment the preservative is selected from the biguanide family of compounds, including but not limited to compounds of the general structure

I and pharmaceutically acceptable salts thereof, where $X_1$ and $X_2$ are hydrogen or any aliphatic, cycloaliphatic, aromatic, substituted aliphatic, substituted aromatic, heteroaliphatic, heterocyclic, or heteroaromatic compound, or a mixture of any of these. $Y_1$ and $Y_2$ are any aliphatic, cycloaliphatic, aromatic, substituted aliphatic, substituted aromatic, heteroaliphatic, heterocyclic, or heteroaromatic compound, or a mixture of any of these. n is an integer equal to or greater than 1, and in typical embodiments, n has an average value such that the molecular weight of the biguanide compounds is about 1000-1400; however, the molecular can be higher or lower. Generally, n is an integer selected from the range of about 2-20. Salts of the compounds of formula I can include salts with an inorganic acid, such as hydrochloride, hydrofluoride, nitrate, sulfate and/or phosphate, and/or salts with an organic acid, such as carboxylic acid, acetate, benzoate, tartrate, adipate, lactate, formate, maleate, glutamate, ascorbate, citrate, gluconate, oxalate, succinate, pamoate, salicylate, isothionate, succinamate, mono-diglycolate, dimethanesulfonate, di-isobutyrate, and/or glucoheptonate. Specific examples of these compounds include, but are not limited to, polyhexamethylene biguanide hydrochloride, p-chlorophenyl biguanide; and 4-chlorobenzhydryl biguanide.

In another aspect of this embodiment, the biguanide compounds include, but are not limited to, halogenated hexidine such as, but not limited to, chlorhexidine (1,1'-hexamethylene-bis-5-(4-chlorophenyl biguanide), alexidine and its salts. The salts include salts with an inorganic acid, such as hydrochloride, hydrofluoride, nitrate, sulfate and/or phosphate, and/or salts with an organic acid, such as carboxylic acid, acetate, benzoate, tartrate, adipate, lactate, formate, maleate, glutamate, ascorbate, citrate, gluconate, oxalate, succinate, pamoate, salicylate, isothionate, succinamate, mono-diglycolate, dimethanesulfonate, di-isobutyrate, and/or glucoheptonate. Examples of salts of chlorhexidine include, but are not limited to, chlorhexidine diphosphanilate, chlorhexidine digluconate, chlorhexidine diacetate, chlorhexidine dihydrochloride, chlorhexidine dichloride, chlorhexidine gluconate, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine di-iodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine monodiglycolate, chlorhexidine dilactate, chlorhexidine di-alpha-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxynaphthoate, and chlorhexidine embonate. Additional examples of biguanide compounds which can be used are disclosed in U.S. Pat. Nos. 2,684,924; 2,990,425; 3,468,898; 4,022,834; 4,053,636; 4,198,392; 6,143,244; 6,143,281; and 6,153,568; EPC 24,031; and DE 1,964,196; DE 2,212,259; and DE 2,627,548, which are incorporated herein by reference.

In another embodiment the preservative is selected from a quaternary ammonium compound of the general formula:

wherein $R_1$, $R_2$, $R_3$, and $R_4$ are independently selected from the group consisting of $C_1$-$C_8$ alkyl, alkylamidoalkyl, ($C_5$-$C_6$ aryl)($C_1$-$C_8$ alkyl), $C_5$-$C_6$ aryl, $C_1$-$C_8$ alkoxy, $C_1$-$C_8$ alkenyl, hydroxyl($C_1$-$C_8$ alkyl), and carboxy($C_1$-$C_8$ alkyl) and X is a negatively charged compound or atom, including for example halides. In one embodiment the quaternary ammonium compound is benzalkonium chloride.

In another embodiment the preservative is selected from a poly quaternary ammonium compound of the general formula:

wherein $R_1$, $R_2$, $R_3$, $R_4$, $R_5$, $R_6$, and $R_7$ are independently selected from the group consisting of H, $C_1$-$C_8$ alkyl, alkylamidoalkyl, ($C_5$-$C_6$ aryl)($C_1$-$C_8$ alkyl), $C_5$-$C_6$ aryl, $C_1$-$C_8$ alkoxy, $C_1$-$C_8$ alkenyl, hydroxyl($C_1$-$C_8$ alkyl), and carboxy ($C_1$-$C_8$ alkyl) and X is a negative atom or compound including a halide. Several examples of bis-quaternary or poly-quanternary ammonium compounds have appeared in the patent and trade literature. U.S. Pat. No. 2,129,264 describes the condensation of "glycerol-di-chlorhydrine" with a tallow dimethyl amine to form a "di-quanternary" ammonium salt. U.S. Pat. No. 2,944,902 describes the conversion of polyethylene glycols with methanesulfonyl chloride to the corresponding bis-ester. Condensation of the bis-ester with a tertiary amine results in the bis-quaternary ammonium salt. U.S. Pat. No. 3,349,032 describes the use of alkylene dihalides or the conversion of bis-tertiary amines with monomeric alkylating agents to bis-quaternary ammonium compounds. U.S. Pat. No. 3,954,633 illustrates the quaternization of tertiary fatty diamines which were prepared from fatty amines by the cyanoethylation route. U.S. Pat. No. 4,110,263 and U.S. Pat. No. 4,181,634 describe the conversion of polyalkylene glycols into bis-alpha,omega-bromoderivatives with phosphorus tribromide and subsequent conversion into the desired bis-quaternary ammonium bromide. In one embodiment the polyquaternary ammonium compound is bis (triethanolammonium chloride) sold under the commercial name "Onamer M" by Stepan Company of Northfield, Ill.

In accordance with one embodiment the biocompatible cleansing solution comprises a biocompatible surfactant, a preservative and an active agent that disrupts the attachment of bacteria to surfaces. More particularly, in accordance with one embodiment the cleansing solution further comprises an agent that disrupts or degrades biofilms produced by various pathogenic bacteria. In one embodiment the cleansing solution further comprises an enzyme that prevents and/or degrades bacterial biofilms. In one embodiment the enzymatic activity is provided by a composition comprising a glycosyl hydrolase and more particularly, an N-acetylglucosaminidase. In one embodiment the N-acetylglucosaminidase is one produced by *Actinobacillus actinomycetemcomitans* and in on embodiment the enzyme is *Actinobacillus actinomycetemcomitans* dispersin B.

In accordance with on embodiment a biocompatible cleansing solution is provided wherein the solution comprises a biocompatible surfactant, selected from the group consisting of polyethylene oxides, polypropylene oxides, polypropylene glycols and polyethylene glycols or co-polymers thereof and a preservative, selected from the group consisting of the biguanide family of compounds, quaternary ammonium compounds and poly quaternary ammonium compounds. Optionally the cleansing solution can further comprising a glycosyl hydrolase, for example an N-acetylglucosaminidase such as *A. actinomycetemcomitans* dispersin B.

In accordance with one embodiment the cleansing solution is provided in a concentrated form, and is packaged in a sterile container and sealed. The container is provided with a sealed opening to allow attachment of the container to a system for diluting and administering the diluted cleansing solution to a surface.

Figure 1:
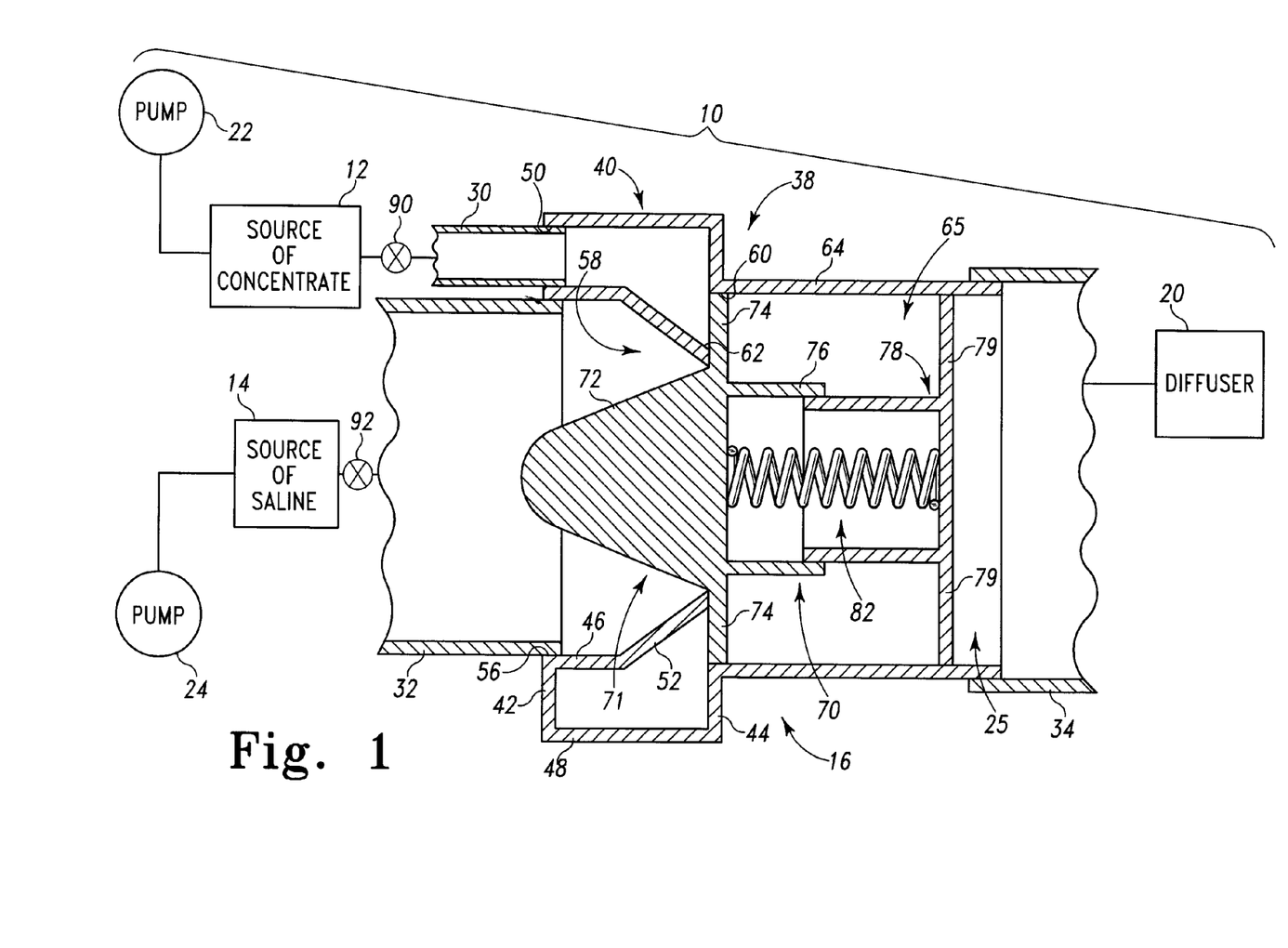
FIG. 1 is a partially schematic, partially cross-sectional view showing a system for decontaminating a wound site including a mixer having a valve member shown in the closed position, a source of concentrate positioned upstream from the mixer, a source of saline positioned upstream from the mixer, and a diffuser positioned downstream from the mixer.
Figure 2:
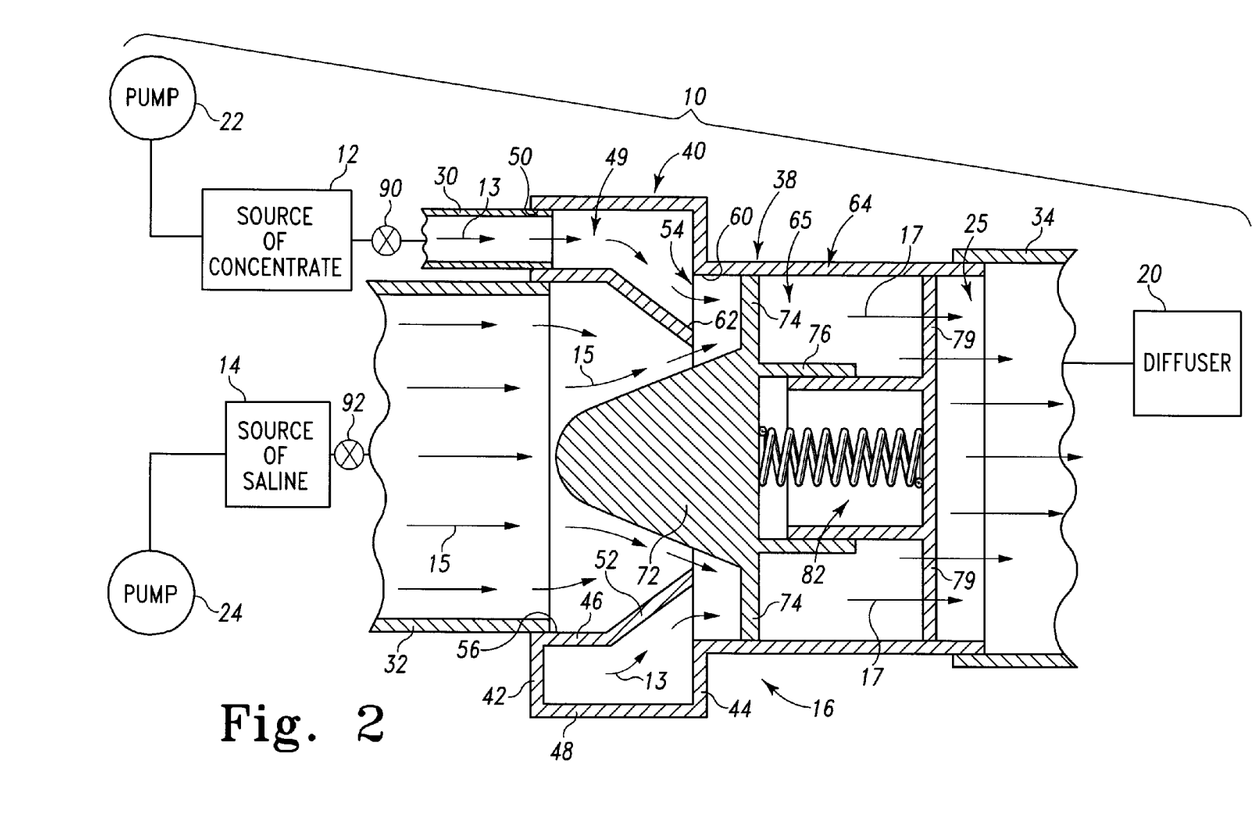
FIG. 2 is partially schematic, partially cross-sectional view of the decontamination system of FIG. 1 showing the valve member of the mixer in an opened position to allow saline and concentrate to flow through and exit the mixer as a combined mixture.

Looking now to FIGS. 1-6, an illustrative system 10 is provided for decontaminating a wound site (not shown). As shown in FIGS. 1 and 2, the system 10 includes a source or receptacle 12 of sterile concentrate or cleansing solution 13, a source or receptacle 14 of sterile saline or saline solution 15, and a mixer 16 in fluid communication with both the receptacles 12, 14. The mixer 16 of the system 10 serves to mix the concentrate (or cleansing solution) 13 with the saline 15 to provide a saline/concentrate mixture 17 for decontaminating the wound site at a point of patient care. As is described in further detail below, the system 10 may also include a diffuser 20 for spraying or diffusing the mixture 17 onto the wound site.

In one embodiment the source 14 of saline 15 may include a typical IV-type saline bag kept on-hand at many hospitals and other areas or points of care where wounds may be treated, fore example. The saline 15 within the saline bag may be placed in fluid communication with the mixer 16 via a standard in line tube fitting that attaches to a standard saline bag. Similarly, the source 12 of the concentrated cleansing solution 13 may be provided with a sealed opening (not shown) to provide fluid communication with the mixer 16 upon breaking or puncturing of the sealed opening.

Further illustratively, the cleansing solution 13 and/or the saline 15 may be pressurized simply through the use of gravity (i.e., the saline may be contained within a standard IV bag and hung from a standard IV pole). Further, the cleansing solution 13 and/or saline 15 may be pressurized by the use of one or more impellers or pumps, such as pumps 22, 24 (shown in FIGS. 1 and 2), that are driven by battery power, electric power, or by an inert gas source, such as a pressurized gas canister, for example. The pumps 22, 24 may be a peristalic pump, a manual pump, and/or an automatic pump and the pressurized flow may be continuous as well as pulsatile. Of course, the means for pressurizing the flow of the saline 15 and/or the cleansing solution 13 may be located upstream or downstream from the respective receptacles 12, 14 and/or may be located upstream or downstream of the mixer 16. Further, as mentioned above, the pressurizing means may include gravity.

As shown in FIGS. 1 and 2, the source 12 of concentrate 13 is fluidly connected to the mixer 16 by a first flexible conduit tube 30 while the source 14 of saline 15 is fluidly connected to the mixer 16 by second flexible conduit tube 32. A third, or exit, flexible conduit tube 34 is coupled to a proximal end of the mixer 16 to receive the concentrate/saline mixture 17 from an outlet 25 of the mixer 16, as shown in FIGS. 1 and 2.

Illustratively, the mixer 16 includes a valve housing 38 defining an annular plenum 40 including a front wall 42, a rear wall 44, and an inner side wall 46 and an outer side wall 48 each coupled to and positioned between the front and rear walls 42, 44 to define an annular space 49 therebetween. A first inlet 50 is defined in the front wall 42 of the annular plenum 40, as shown in FIGS. 1-4. Illustratively, the first 30 conduit tube is received within the first inlet 50 of the annular plenum 40 provide communication between the source of concentrate 12 and the annular space 49. The inner side wall 46 of the annular plenum 40 further defines a plurality of radially spaced-apart angled spokes or wall portions 52 each defining a passageway 54 in communication with the annular space 49. Looking now to FIG. 4, the inner side wall 46 of the annular plenum 40 defines a second inlet 56. Illustratively, the second conduit tube 32 is received within the second inlet 56 to provide communication between the source 14 of saline 15 and a saline passageway 58 of the annular plenum 40.

Figure 4:
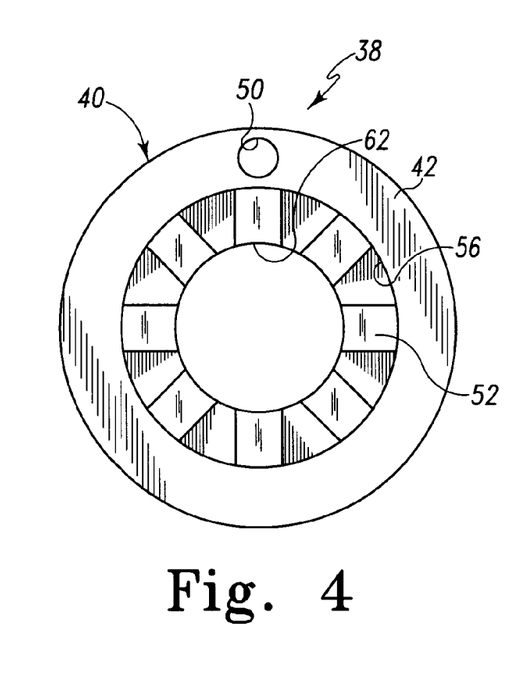
FIG. 4 is a front view of the valve housing of the mixer shown in FIGS. 1-3.
Figure 6:
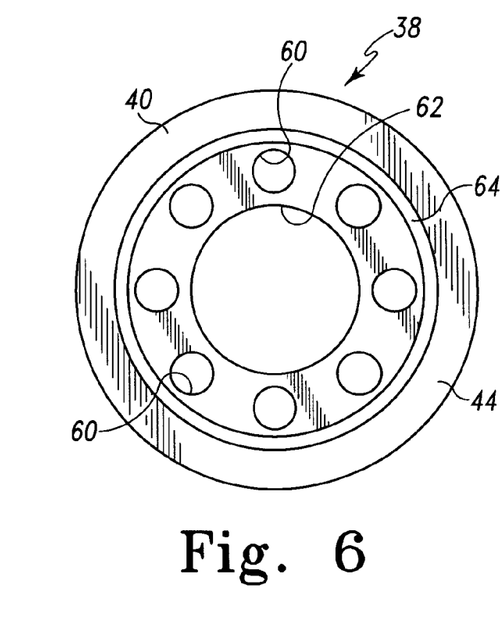
FIG. 6 is a rear view of the valve member of the mixer shown in FIGS. 1-4.

As shown in FIG. 6, the rear wall 44 of the annular plenum 40 includes a plurality of first discharge ports 60 formed therein and a second discharge port 62. The first discharge ports 60 are each in communication with the annular space 49 of the annular plenum 40 whereas the second discharge port 62 is in communication with the saline passageway 58, the second inlet 56, and the source 14 of saline 15. The first discharge ports 60 are positioned annularly around the second discharge port 62. Although a plurality of discharge ports 60 is disclosed, it is within the scope of this disclosure to include an annular plenum having only one first discharge port formed therein. Illustratively, the angled spokes 52 of the annular plenum 40 cause the saline passageway 58 to narrow when moving in an upstream direction. As such, the second discharge port 62 is smaller than the second inlet 56, as shown in FIGS. 1, 2, and 4, for example.

Figure 3:
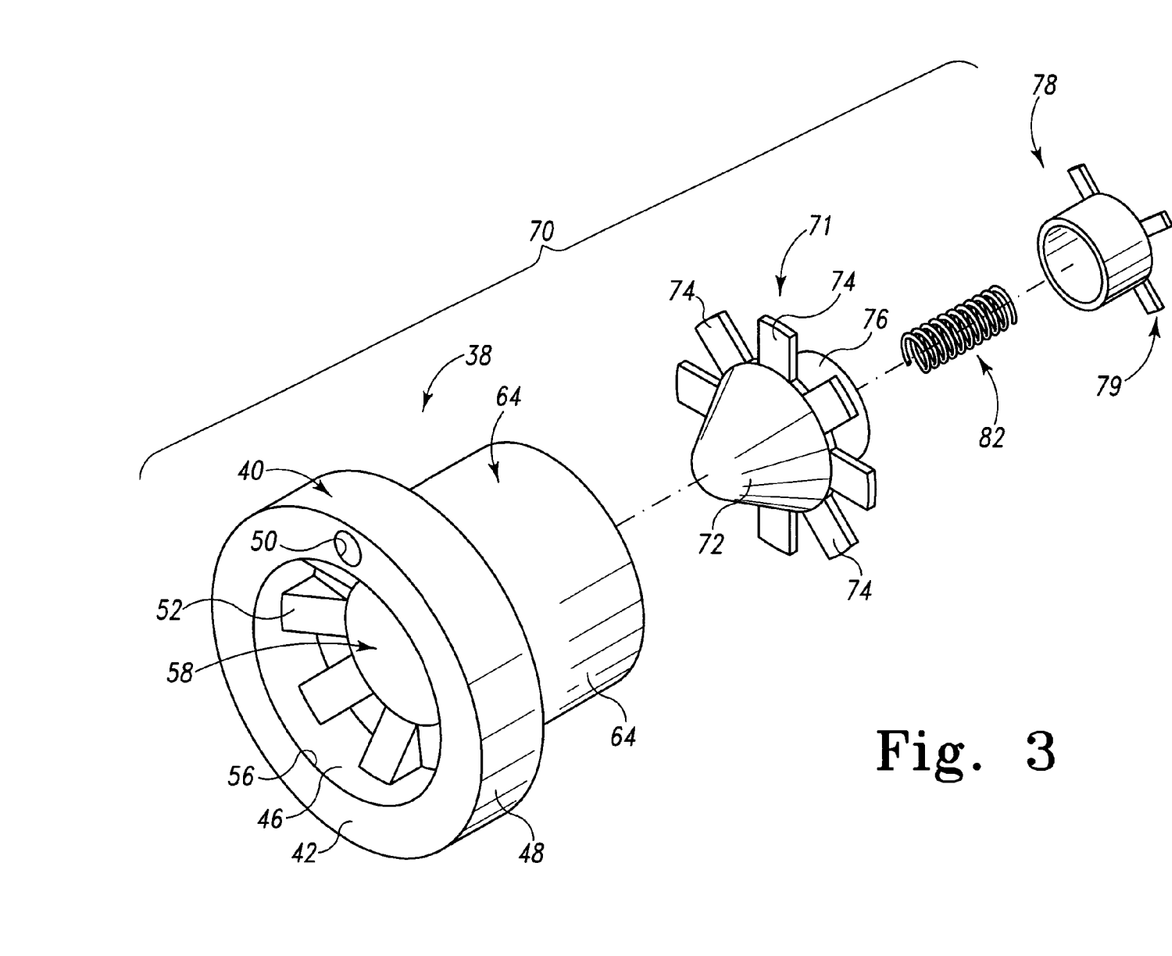
FIG. 3 is an exploded, perspective view of the mixer of the decontamination system shown in FIGS. 1 and 2 showing the mixer including a valve housing, the valve member, a coil spring, and an end cap, and further showing the valve member including a cone-shaped diverter and flanges extending radially outwardly from the diverter.
Figure 5:
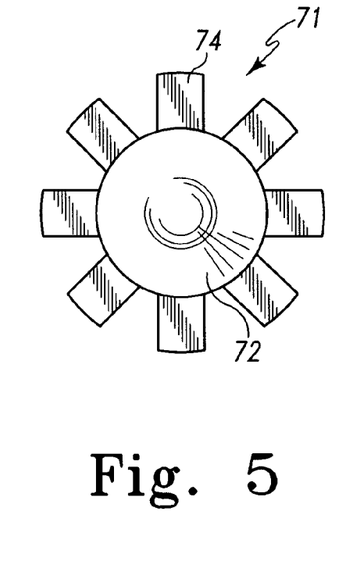
FIG. 5 is a front view of the valve member of the mixer shown in FIGS. 1-3.

The valve housing 38 of the mixer 16 further includes a mixing conduit 64 coupled to the rear wall 44 of the annular plenum 40, as shown in FIGS. 1 and 2 and formed to define a mixing chamber 65 and the outlet 25 of the mixer 16 positioned downstream of the mixing chamber 65. The annular plenum 40 and the mixing conduit 64 may be modular components of the valve housing 38 coupled together to form a generally water-tight seal, or may be formed as a single, unitary structure, as shown in FIGS. 1-3. Illustratively, both the first discharge ports 60 and the second discharge port 64 exit into the mixing chamber 65 of the mixing conduit 64, as shown in FIG. 5. The mixing conduit 64 is then coupled to the third flexible conduit 34 to provide communication between the mixing chamber 65 and the diffuser or sprayer 20, as is discussed in greater detail below.

A valve assembly 70 of the mixer 16 is shown in FIGS. 1-3 and 5 and is positioned within the annular plenum 40 and the mixing conduit 64 of the mixer 16. Illustratively, as shown in FIGS. 1-3, the valve assembly 70 includes a valve member 71 having a cone-shaped diverter 72, a plurality of flanges or blades 74 extending radially from a base end of the diverter 72, and an annular flange 76 extending rearwardly from the base end of the diverter 72. An end cap 78 of the valve assembly 70 is received within the annular flange 76, as shown in FIGS. 1 and 2. Several struts 79 of the valve assembly 70 extend outwardly from the end cap 78 to secure the end cap 78 to the mixing conduit 64 of the valve housing 38. The radial struts 79 of the valve assembly 70 are provided as a coupling mechanism to couple the end cap 78 to the valve housing 38. As such, the struts 79 are illustrative in nature and it is within the disclosure to include any suitable coupling mechanism for coupling the end cap 78 to the valve housing 38 while providing fluid flow passageways around and past the end cap 78. A spring 82 is positioned between the end cap 80 and the cone-shaped diverter 72.

Illustratively, the spring 82 allows the valve assembly 70 to move between a closed position, as shown in FIG. 1, and an opened position, as shown in FIG. 2. In the closed position, the cone-shaped diverter 72 is received generally entirely through the second discharge port 62 of the annular plenum 40 to block or close the second discharge port 62 (and therefore the second inlet 56) to prevent saline 15 from flowing through the annular plenum 40 and into the mixing chamber 65. Illustratively, a tip end of the cone-shaped diverter 72 may extend through the second inlet 56 of the annular plenum 40. Further, the radially-extending blades 74 of the valve member 71 close or cover the first discharge ports 60 when the valve member 71 is in the closed position to prevent the cleansing solution 13 from flowing therethrough. The blades 74 of the valve member 71 may be provided with washers or other sealing structures to assist in sealing the first discharge outlets 60 when the valve member 71 is in the closed position. Further illustratively, the valve member 71 of the valve assembly 70 includes eight blades 74 to block or cover the eight discharge ports 60 formed in the rear wall 44 of the annular plenum 40. It is within the scope of this disclosure, however, to include a plenum having any suitable number of first discharge ports and a corresponding valve member having any number of blades to block or close the discharge ports. The coil spring 82 operates to bias the valve member 71 of the valve assembly 70 to the closed position to close or block the first and second discharge ports 60, 62.

The valve assembly 70 may be moved to the opened position by moving the cone-shaped diverter 72 to the right, as shown in FIG. 2, against the bias of the coil spring 82. For example, sufficient saline flow through the second inlet 56 exerts pressure on the diverter 72 of the valve member 71 to overcome the biasing force of the spring 82 to move the valve member 71 of the valve assembly 70 to the opened position, as shown in FIG. 2. Illustratively, the bias of the spring 82 may be sufficient to counteract the load of the saline when the saline is stagnant or static and is not actively flowing through the system. As such, once saline flow begins, by opening the diffuser 20, for example, the pressure of the dynamic flow of the saline 15 on the diverter 72 overcomes the bias of the coil spring 82 to move the valve member 71 to the opened position and the second discharge port 62 of the annular plenum 40 opens to allow the saline 15 to flow therethrough into the mixing chamber 65. Alternatively, the diverter 72 of the valve member 71 may be sized to permit saline 15 to flow through the discharge port 62 when the valve member 71 is in the closed position. In either embodiment, movement of the valve member 71 to the opened position through the force exerted on the valve member 71 by the saline 15 disengages the blades 74 of the valve member 71 from the rear wall 44 of the annular plenum 40. Once the blades 74 are spaced-apart from the rear wall 44, the cleansing solution 13 is allowed to flow into the mixing chamber 65 to mix with the saline 15 also flowing into the mixing chamber 65 to create the saline/concentrate mixture 17.

Further, as the saline 15 is advanced through the second conduit tube 32 and into the saline passageway 58, the cone-shaped diverter 72 causes the saline 15 to move outwardly within the passageway 58 to create an outward, annular flow of the saline 15 within the saline passageway 58. In other words, the diverter 72 forces the central saline flow towards the outer periphery of the saline passageway 58 near the inner wall 46 of the annular plenum 40. Further, the diverter 72 may cause the saline 15 to accelerate past the first discharge ports 60 to create a venturi effect to draw the concentrated cleansing solution 13 out from the first receptacle 12. The second inlet port 56 and the second discharge port 62 may be sized and positioned relative to the first inlet port 50 and the first discharge ports 60 to create a venturi or siphoning effect to assist in, or provide the sole force of, pulling the cleansing solution concentrate 13 into the mixer 16 to mix with the saline 15 and provide the desired mixing ratio between the cleansing solution 13 and the saline 15.

Illustratively, the valve member 71 moves between the opened and closed positions along an axis parallel with the generally axial flow of the saline 15 into the mixer 16. Illustratively, the diameter of a base portion of the diverter 71 may be smaller than the second discharge port 62 of the annular plenum 40 to permit saline to 15 flow around the diverter 72 and into the mixing chamber 65 when the valve assembly 70 is in the closed position. Illustratively, a diameter of the base portion of the diverter 72 may be approximately 50%-60% a diameter of the second discharge port 62. As such, saline 15 flowing at a reduced pressure less than that required to overcome the spring-bias of the coil spring 82 may allow the valve assembly 70 to remain in the closed position to block fluid flow of the cleansing solution 13 into the mixing chamber 65 while permitting saline 15 to flow into the mixing chamber 65. Of course, increasing the pressure of the saline solution 15 to overcome the spring-bias of the spring 82 will move the valve member 71 to the opened position to allow the cleansing solution 13 to flow into the mixing chamber 65, as discussed above.

Illustratively, the first discharge ports 60 and the second discharge port 62 may be sized to maintain a desired mixing ratio between the concentrate 13 and the saline 15. Reducing or stopping the flow of saline 15 through the mixing chamber 65 reduces the pressure of the saline 15 exerted on the valve member 71 of the valve assembly 70 such that the spring 82 is able to move the valve member 71 of the valve assembly 70 to the closed position. Although the spring 82 is a coil spring, it is within the scope of this disclosure for the valve assembly 70 to include another suitable spring, such as a helical spring, elastic bands, etc.

Looking again to FIGS. 1 and 2, a first on/off or bypass valve 90 may be provided downstream from the source 12 of concentrate 13 to control the flow of concentrate 13 through the first conduit tube 30. Similarly, a second on/off or bypass valve 92 may be provided downstream from the source 14 of saline 15 to control the flow of saline 15 through the second conduit tube 32. These on/off valves 90, 92 may be controlled manually and/or automatically. Further, the first on/off valve 90 may be adjusted to an on/off position to prevent the flow of the concentrate 13 into the mixer 16 and allow only the saline 15 to flow through the mixer 16 to be applied to the wound site. Further, the flow of the saline 15 from the saline source 14 and/or the concentrate 13 from the concentrated source 12 also may each be monitored by a meter (not shown) and regulated by metered valves, impellers (not shown), and/or the use of metered orifices sized to provide the desired flow rate.

Illustratively, the source 12 of concentrated cleansing solution 13 may be integrally coupled to the mixer 16 or may be coupled to the mixer via a flexible conduit tube, such as tube 30, for example. For example, the source of concentrated cleansing solution 12 may be attached to the mixer 16 by molding or physically sealing the source 12 of the concentrated cleansing solution 13 directly to the mixer 16. As such, the cleansing solution source 12 may be provided with a flow channel (not shown) able to be coupled directly to the mixer 16. Alternatively, the source 12 of concentrated cleansing solution 13 may be provided as a modular component, wherein its contents (i.e., the concentrate 13) are placed in fluid communication with the mixer 16 via standard flexible tubing or other suitable conduit. The tubing may further be provided with components for forming a water tight seal with both the source of concentrated cleansing solution 12 and the mixer 16, using standard techniques known to the skilled practitioner. For example the flexible tubing may be attached to the concentrate source 12 using threads, luer (bayonet type) fittings, or other physical mounts to hold the concentrate source 12 in fluid communication with the mixing chamber 16. Further, attaching the flexible tubing to the concentrate source 12 may include breaking a seal (not shown) of the concentrate source 12 to create a flow channel to the mixing chamber 16.

The mixer 16 may further include vanes, baffles, tubes or other components (not shown) within the mixing chamber 65 to enhance turbulence of the saline/cleansing solution mixture 17 and thus enhance the mixing of the saline 15 with the cleansing solution 13 prior to advancing the mixture 17 through the outlet 25 of the mixer 16. This downstream rotation within the mixing chamber 65 further combines and more evenly distributes the saline 15 and the cleansing solution 13 within the mixture 17. The vanes, baffles, or tubes may be radially positioned within the mixing chamber of the mixer 16 and coupled to the mixing conduit 64 of the mixer 16. The downstream rotation may be imparted by forcing the annular flow through the series of vanes, baffles, or tubes. Further, the vanes, baffles, or tubes may be orientated at an angle to the annular flow of the mixture 17.

Illustratively, it is within the scope of this disclosure for the various inlets, outlets, and discharge ports of the mixer 16 of the present decontamination system 10 to be formed having various shapes. As shown in FIGS. 3-6, the first and second inlets 50, 56, the first and second discharge ports 60, 62, and the outlet 25 are each generally circular in shape. However, each may be formed to define any other suitable shape. Illustratively, the first and second inlets 50, 56 of the mixer 16 and the outlet 25 of the mixer 16 are formed to frictionally receive a tube or tubing, such as tubes 30, 32, 34 inserted into the respective inlet 50, 56 and/or outlet 25. Alternatively, an annular projection (not shown) may extend outwardly from the valve housing around each of the first and second inlets 50, 56 of the mixer 16 and the outlet 25 to provide a means for attaching a tube over the projection to frictionally engage the projection.

As mentioned above, the system 10 may include a diffuser 20 such as a nozzle, irrigation device, and/or sprayer, for example. Illustratively, the diffuser 20 operates to effectively diffuse, disperse, and/or spray the saline/cleansing mixture 17 onto a wound site. The flexible conduit tubing 34 provides fluid communication between the mixer 16 and the irrigation device or diffuser 20. Illustratively, the diffuser may include an on/off valve (not shown) to prevent fluid from flowing therethrough. Closing this valve may create a back pressure which impedes fluid flow of the saline 15 and cleansing solution 13 through the mixer 16. Further illustratively, the diffuser 20 may include various detachable nozzles heads (not shown) having different nozzle designs to provide different flow stream shapes and velocities and to enable appropriate access and/or coverage of the mixture 17 to the wound site for various clinical situations.

In accordance with another embodiment, the system 10 may further include an aspirator (not shown) which may be provided to remove pooled fluids which have accumulated at the surface of the wound site to be cleaned. Further illustratively, the diffuser or irrigation device may be provided with fittings that allow attachment of the aspirator to the irrigation device. Alternatively, the aspirator may be permanently fixed to the irrigation device. For example, the aspirator may be fixed to the irrigation device such that a tip of the aspirator extends forwardly beyond a nozzle of the irrigation device to allow the aspirator to remove liquids from cavities or space within the wound site without interference from the nozzle. Illustratively, the system 10 may further include a switch (not shown) mechanically or electronically connected to valves (not shown) that regulate flow of the saline/cleansing solution mixture 17 through the irrigation device and aspirator. Use of this switch allows for operation of either the irrigation device or aspirator by itself, or the simultaneous use of both the irrigation device and aspirator, for example.

Illustratively, it is also within the scope of this disclosure to provide a kit for disinfecting and cleansing a surgical wound. The kit may include the biocompatible cleansing solution described herein and the sterile mixer 16. The kit may further include a plurality of sterile, flexible conduit tubing, such as tubes 30, 32, 34, for example.

In one embodiment of the present disclosure, a method for decontaminating a wound comprises administering a biocompatible cleansing solution consisting essentially of a biocompatible surfactant and a preservative. In another embodiment the method comprises administering a biocompatible cleansing solution consisting essentially of a biocompatible surfactant and a preservative. In one embodiment the biocompatible surfactant is selected from the group consisting of polyethylene oxides, polypropylene oxides, polypropylene glycols and polyethylene glycols or co-polymers thereof, and the preservative or antimicrobial agent is selected from the group consisting of the biguanide family of compounds, quaternary ammonium compounds and poly quaternary ammonium compounds.

While the concepts of the present disclosure have been illustrated and described in detail in the drawings and foregoing description, such an illustration and description is to be considered as exemplary and not restrictive in character, it being understood that only the illustrative embodiments have been shown and described and that all changes and modification that come within the spirit of the disclosure are desired to be protected.

There are a plurality of advantages of the present disclosure arising from the various features of the solution, apparatus, and methods described herein. It will be noted that alternative embodiments of the solution, apparatus, and methods of the present disclosure may not include all of the features described, yet still benefit from at least some of the advantages of such features. Those of ordinary skill in the art may readily devise their own implementations of an apparatus and method that incorporate one or more of the features of the present disclosure and fall within the spirit and scope of the present disclosure.

The invention claimed is:

1. A system for decontaminating a wound site, the system comprising:
   a mixer including a first inlet, a second inlet, a mixing chamber positioned downstream from the first and second inlets, and an outlet positioned downstream from the mixing chamber;
   a sterile, biocompatible cleansing solution contained in a first receptacle, the first receptacle being in fluid communication with the first inlet of the mixer;
   a sterile saline solution contained in a second receptacle, the second receptacle being in fluid communication with the second inlet of the mixer; and
   a diffuser in fluid communication with the outlet of the mixer,
   wherein the mixer further includes a spring-biased valve member movable between (i) a closed position preventing fluid communication between the mixing chamber and the first inlet to prevent the sterile, biocompatible cleansing solution from entering the mixing chamber and (ii) an opened position permitting fluid communication between the mixing chamber and the first inlet to permit the sterile, biocompatible solution to enter the mixing chamber, and the valve member includes a cone-shaped diverter to close the second inlet when the valve member is in the closed position and a flange extending outwardly from the diverter to close the first inlet when the valve member is in the closed position.

2. A system for decontaminating a wound site, the system comprising:
   a mixer including a first inlet, a second inlet, a mixing chamber positioned downstream from the first and second inlets, and an outlet positioned downstream from the mixing chamber;
   a sterile, biocompatible cleansing solution contained in a first receptacle, the first receptacle being in fluid communication with the first inlet of the mixer;
   a sterile saline solution contained in a second receptacle, the second receptacle being in fluid communication with the second inlet of the mixer; and
   a diffuser in fluid communication with the outlet of the mixer,
   wherein:
   (i) the mixer includes a valve housing having an annular plenum defining an annular space and a mixing conduit coupled to the annular plenum to define the mixing chamber, and
   (ii) the first inlet is formed in a front wall of the annular plenum.

3. The system of claim 2, wherein the annular plenum includes an inner wall defining a central aperture and the central aperture is the second inlet.

4. The system of claim 2, wherein the annular plenum further includes a plurality of hollow spokes in fluid communication with the annular space.

5. The system of claim 2, wherein the annular plenum further includes a rear wall defining a first discharge port in communication with the mixing chamber.

6. The system of claim 5, wherein the annular plenum includes a plurality of discharge ports defined in the rear wall.

* * * * *